(12) United States Patent
Chiang

(10) Patent No.: US 10,206,819 B2
(45) Date of Patent: Feb. 19, 2019

(54) SWIMMING GOGGLE CUSHION PAD

(71) Applicant: Global Esprit Inc., New Taipei (TW)

(72) Inventor: Herman Chiang, New Taipei (TW)

( * ) Notice: Subject to any disclaimer, the term of this patent is extended or adjusted under 35 U.S.C. 154(b) by 420 days.

(21) Appl. No.: 15/134,378

(22) Filed: Apr. 20, 2016

(65) Prior Publication Data

US 2017/0290706 A1    Oct. 12, 2017

(30) Foreign Application Priority Data

Apr. 12, 2016 (TW) .............................. 105205095 U

(51) Int. Cl.
*A61F 9/02* (2006.01)
*A63B 33/00* (2006.01)

(52) U.S. Cl.
CPC ............. *A61F 9/026* (2013.01); *A63B 33/002* (2013.01); *A63B 2033/004* (2013.01)

(58) Field of Classification Search
CPC ........ A42B 3/283; A63B 33/002; A61F 9/026
USPC .................................................... 2/428, 440
See application file for complete search history.

(56) References Cited

U.S. PATENT DOCUMENTS

| 5,331,691 | A | * | 7/1994 | Runckel | ............... | A63B 33/002 |
| | | | | | | 2/428 |
| 7,647,650 | B2 | * | 1/2010 | Chiang | ............... | A63B 33/002 |
| | | | | | | 2/426 |
| 2002/0178489 | A1 | * | 12/2002 | Sung | ................... | A63B 33/002 |
| | | | | | | 2/428 |
| 2015/0374550 | A1 | * | 12/2015 | Saylor | .................... | A61F 9/028 |
| | | | | | | 2/436 |
| 2017/0252609 | A1 | * | 9/2017 | Chiang | ............... | A63B 33/002 |

* cited by examiner

Primary Examiner — Katherine M Moran

(57) ABSTRACT

The present invention is to provide a swimming goggle swimming goggle cushion pad in contact with a wearer's face around the eye socket, comprising: a connection frame defined with an inner peripheral face and an outer peripheral face, a circumferential fitting groove mounted between the inner peripheral face and the outer peripheral face to receive a circumference of the swimming goggle frame; a face contact portion extending along the inner peripheral face of the connection frame and defined with an outer ring surface and an inner ring surface; a buffer unit disposed between the inner peripheral face of the connection frame and the outer ring surface of the face contact portion; wherein the buffer unit provides the face contact portion with support and restoring forces against a deformation stress produced between the cushion pad and the wearer's face when worn, to ensure a comfortable engagement with the wearer's face skin.

11 Claims, 20 Drawing Sheets

SWIMMING GOGGLE CUSHION PAD

CROSS REFERENCE TO RELATED APPLICATIONS

This non-provisional application claims priority under 35 U.S.C. § 119(a) on Patent Application Ser. No. 105205095 filed in Taiwan on Apr. 12, 2016, the entire contents of which are hereby incorporated by reference.

BACKGROUND OF THE INVENTION

Field of the Invention

The present invention relates to a swimming goggle cushion pad, and particularly to a swimming goggle cushion pad capable of buffering the stress or pressure acted on a wearer's face around the eye socket when worn, to ensure a comfortable engagement with the wearer's face skin without water leakage.

Description of the Related Art

As well known, swimming goggles are usually provided with cushion pads to be in contact with the wearer's face around the eye socket for a desired water leakage proof effect. However, the wearer's face around the eye socket has an irregular surface contour of which a facial part near the eyebrow bulges outward while a facial part near the zygomatic bone slightly draws back inward. The cushion pads, whether being of foam type or suction cup type, are necessary to be pushed hard enough against the wearer's face around the eye socket when worn to tightly fit into the irregular surface contour thereof, otherwise the engagement with the wearer's face around the eye socket would be insufficient, especially the insufficient engagement with the facial part corresponding to the zygomatic bone, which may lead to water leakage. Still, when the cushion pads are being pushed against the wearer's face around the eye socket, a deformation stress is thus produced therebetween, which may cause an uncomfortable contact between the cushion pads and the wearer's face.

Particularly, the suction cup type cushion pads seem more likely to cause such deformation stress onto the wearer's eye socket due to their excellent air suction property and therefore the panda eyes may come out in taking off the swimming goggles. An example of conventional swimming goggles comprising a suction cup type cushion pad 5 is shown in FIGS. 1A to 1D. As shown, the suction cup type cushion pad 5 comprises a connection frame 50 and a face contact portion 51. The connection frame 50 is mounted with a circumferential fitting groove 501 to connect a swimming goggle frame (not shown) therewith. The face contact portion 51 is defined with an outer ring surface 511 and an inner ring surface 512 in opposite to the outer ring surface 511. The inner ring surface 512 adheres to the wearer's face around the eye socket upon the collapse of the outer ring surface 511. The outer ring surface 511 upon collapse may cause the deformation stress onto the eye socket due to the air suction inside the swimming goggles and thus cause the uncomfortable contact between the suction cup type cushion pad 5 and the wearer's face. At present, it is still an unresolved issue of how to improve the suction cup type cushion pad 5 to avoid the mentioned problems of the conventional swimming goggles.

BRIEF SUMMARY OF THE INVENTION

Accordingly, an object of the present invention is to provide a swimming goggle cushion pad of the suction cup type adapted to absorb such deformation stress which is directly acted on a wearer's face around the eye socket when worn to ensure a comfortable engagement with the wearer's face skin without water leakage.

To achieve the above-mentioned object, the swimming goggle cushion pad of the present invention is connected to a swimming goggle frame and adapted to be in contact with a wearer's face around the eye socket, wherein the swimming goggle cushion pad comprises: a connection frame defined with an inner peripheral face and an outer peripheral face, a circumferential fitting groove being mounted between the inner peripheral face and the outer peripheral face to receive a circumference of the swimming goggle frame; a face contact portion extending along the inner peripheral face of the connection frame and defined with an outer ring surface and an inner ring surface; a buffer unit disposed between the inner peripheral face of the connection frame and the outer ring surface of the face contact portion; wherein the buffer unit provides the face contact portion with support and restoring forces against a deformation stress produced between the cushion pad and the wearer's face when worn.

In accordance with the present invention, the buffer unit comprises a plurality of compartments each surrounded by two support ribs and a plurality of peripherals to form an opening, wherein the compartments and the opening work together to provide the face contact portion with support and restoring forces against a deformation stress produced between the cushion pad and the wearer's face when worn.

In accordance with the present invention, alternatively, the buffer unit comprises a plurality of a plurality of support ribs and a plurality of openings between each two adjacent support ribs, wherein the support ribs and the openings work together to provide the face contact portion with support and restoring forces against the deformation stress produced between the cushion pad and the wearer's face when worn.

In accordance with the present invention, the swimming goggle cushion pad fitting to an irregular surface contour of the eye socket of the wearer has an axial length corresponding to the eyebrow of the wearer measured from the connection frame to the buffer unit to the face contact portion smaller than an axial length corresponding to the zygomatic bone of the wearer also measured from the connection frame to the buffer unit to the face contact portion, so as to ensure a compliant engagement with the irregular surface contour of the eye socket of the wearer.

In accordance with the present invention, the support ribs and the openings scattering at a circumferential direction of the buffer unit are arranged partially at a top half of the buffer unit corresponding to the eyebrow of the wearer and fully at a bottom half of the buffer unit corresponding to the zygomatic bone of the wearer.

In accordance with the present invention, the support ribs and the openings at the top half of the buffer unit corresponding to the eyebrow of the wearer are smaller and fewer than the support ribs and the openings at the bottom half of the buffer unit corresponding to the zygomatic bone of the wearer.

Further in accordance with the present invention, the support ribs and the openings scattering at the circumferential direction of the buffer unit have different sizes, for example, the support ribs and the openings become longer and wider gradually at a direction from an inner part of the buffer unit corresponding to a nose bridge of the wearer to an outer part of the buffer unit corresponding to an outer eye corner of the wearer.

DETAILED DESCRIPTION OF THE INVENTION

Figure 1A:
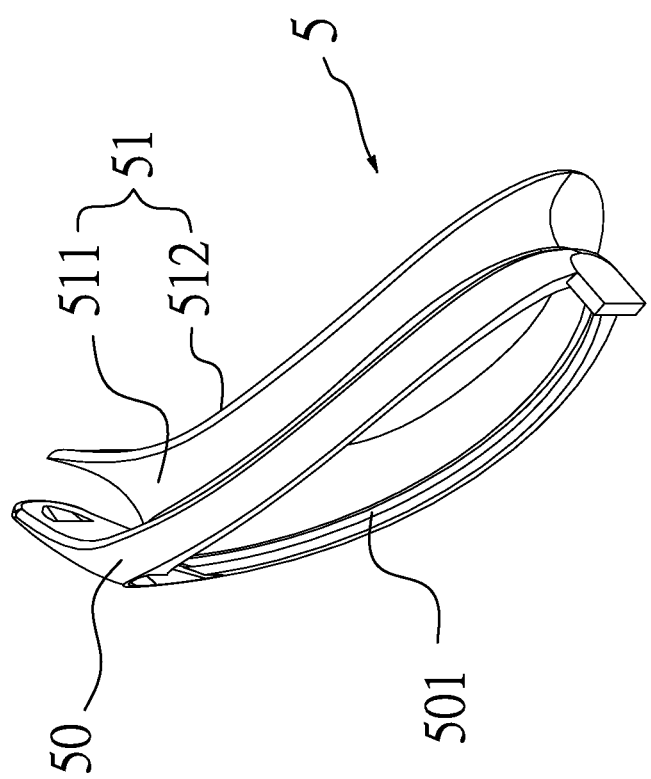
FIGS. 1A to 1D respectively are a perspective view, a top view, a front view and a cross-sectional view of a conventional swimming goggle cushion pad.
Figure 1B:
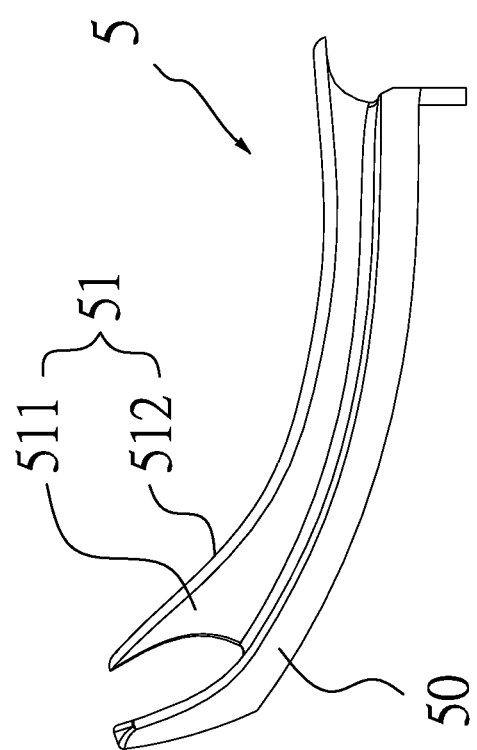
Figure 1C:
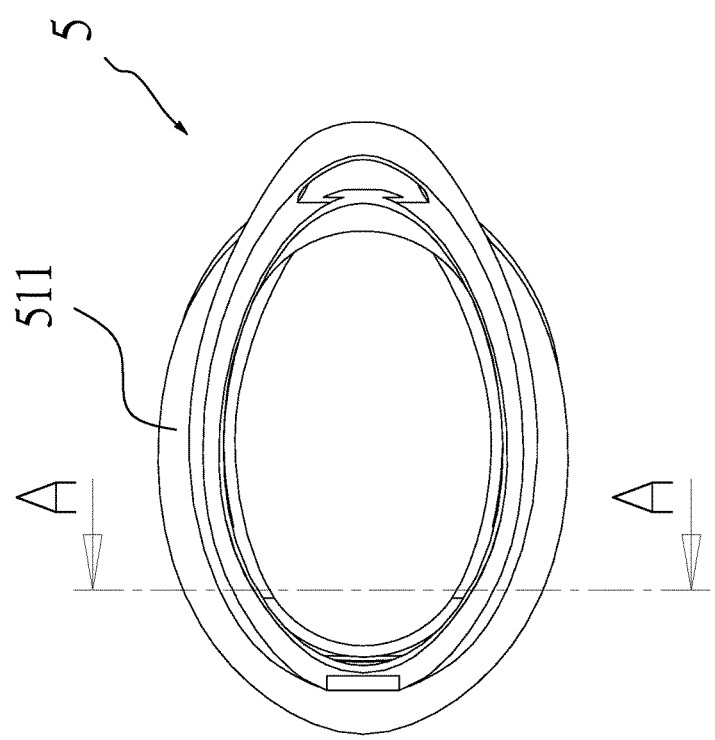
Figure 1D:
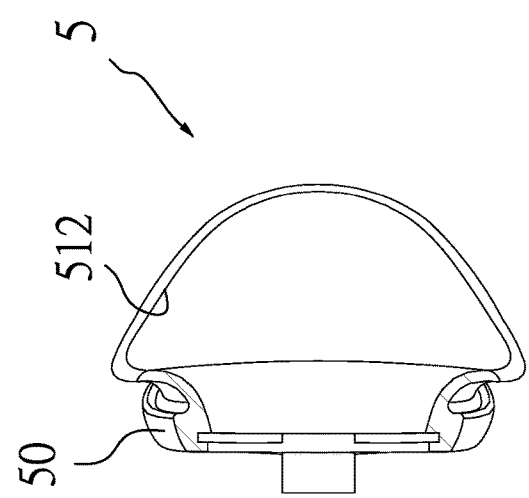
Figure 2:
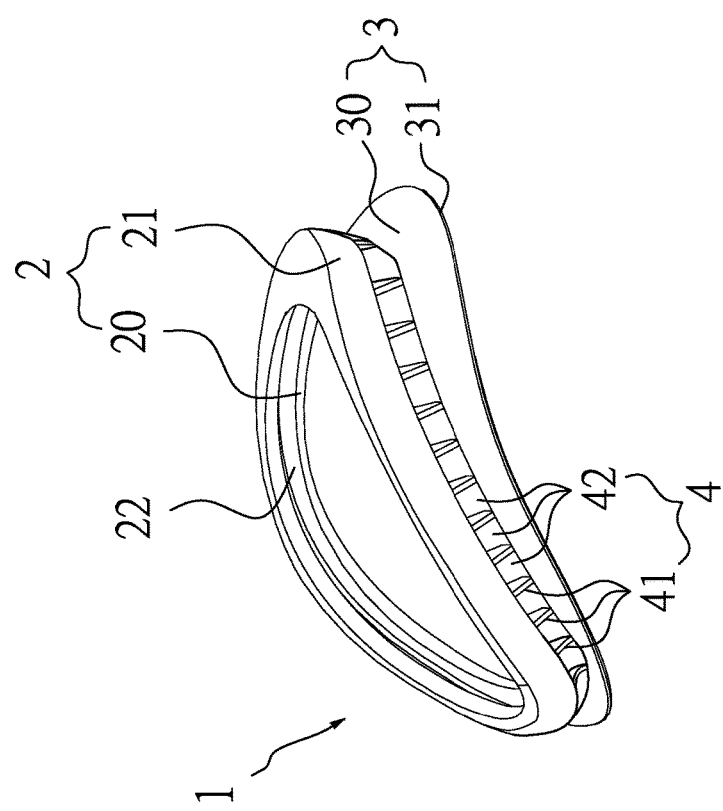
FIG. 2 is a perspective view of a first embodiment of the present invention.
Figure 7:
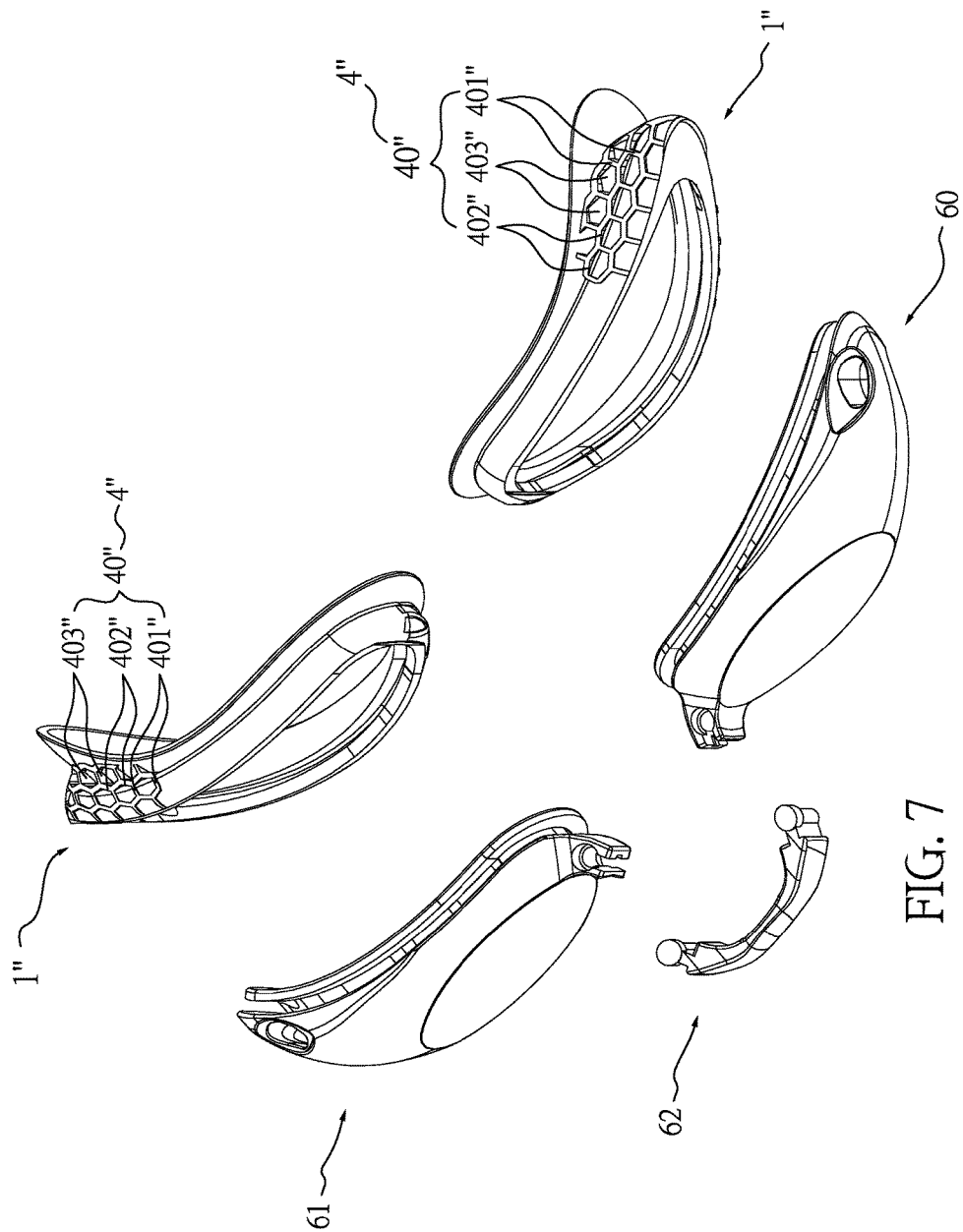
FIG. 7 is a an exploded perspective view of the swimming goggle cushion pad of the present invention together with left and right frames and a connecting element of a swimming goggles.

With reference to FIG. 2, which shows a first embodiment in accordance with the present invention, a cushion pad 1 of the first embodiment in accordance with the present invention made of thermo plastic rubber or silicon, includes a connection frame 2, a face contact portion 3 and a buffer unit 4. The connection frame 2 connected to a swimming goggle frame, as shown in FIG. 7, is defined with an inner peripheral face 20 and an outer peripheral face 21. A circumferential fitting groove 22 is mounted between the inner peripheral face 20 and the outer peripheral face 21, adapted to receive a circumference of the swimming goggle frame. The face contact portion 3 extending along the inner peripheral face 20 of the connection frame 2 is defined with an outer ring surface 30 and an inner ring surface 31. The inner ring surface 31 is adapted to be in contact with an eye socket of a wearer. The buffer unit 4 is disposed between the inner peripheral face 20 of the connection frame 2 and the outer ring surface 30 of the face contact portion 3. In this embodiment, the buffer unit 4 in accordance with the present invention comprises a plurality of support ribs 41 arranged at intervals, and a plurality of openings 42 each formed between adjacent support ribs 41. The support ribs 41 and the openings 42 work together to provide the face contact portion 3 with support and restoring forces against a deformation stress produced between the cushion pad 1 and the wearer's face when the cushion pad 1 is worn. Thus, the buffer unit 4 functioned as a buffer is adapted to absorb the deformation stress which is directly acted on a wearer's face around the eye socket when worn, so as to ensure a comfortable engagement with the wearer's face skin without water leakage.

Figure 3:
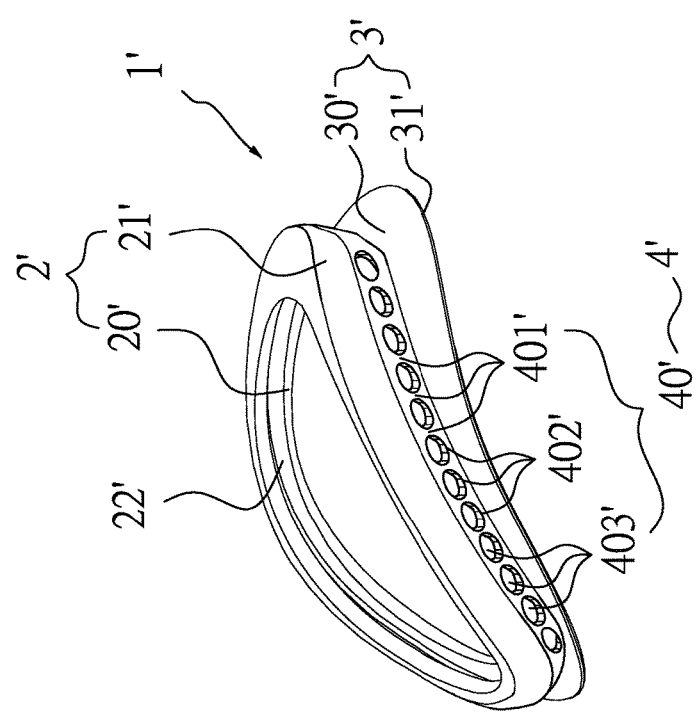
FIG. 3 is a perspective view of a second embodiment of the present invention.

With reference to FIG. 3, which shows a second embodiment in accordance with the present invention, a cushion pad 1' of the second embodiment in accordance with the present invention made of thermo plastic rubber or silicon as well, includes a connection frame 2', a face contact portion 3' and a buffer unit 4'. The connection frame 2' adapted to connect with a swimming goggle frame which is shown in FIG. 7 is defined with an inner peripheral face 20' and an outer peripheral face 21'. A circumferential fitting groove 22' is mounted between the inner peripheral face 20' and the outer peripheral face 21', adapted to receive a circumference of the swimming goggle frame. The face contact portion 3' extending along the inner peripheral face 20' of the connection frame 2' is defined with an outer ring surface 30' and an inner ring surface 31'. The inner ring surface 31' is adapted to be in contact with an eye socket of a wearer. The buffer unit 4' is disposed between the inner peripheral face 20' of the connection frame 2' and the outer ring surface 30' of the face contact portion 3'. In this embodiment, the buffer unit 4' in accordance with the present invention comprises a plurality of compartments 40' each surrounded by two support ribs 401' and a plurality of peripherals 402' to form an opening 403' with a geometric shape, such as ellipse, rectangle, polygon, etc. The compartments 40' of the buffer unit 4' in this embodiment are composed of a plurality of elliptical openings 403' as being of elliptical type. The compartments 40' and the openings 403' work together to provide the face contact portion 3' with support and restoring forces against a deformation stress produced between the cushion pad 1' and the wearer's face when the cushion pad 1' is worn, to provide a comfortable engagement with the wearer's face skin without water leakage. Thus, the buffer unit 4' functioned as a buffer is adapted to absorb the deformation stress which is directly acted on a wearer's face around the eye socket when worn, so as to ensure a comfortable engagement with the wearer's face skin without water leakage.

Figure 4A:
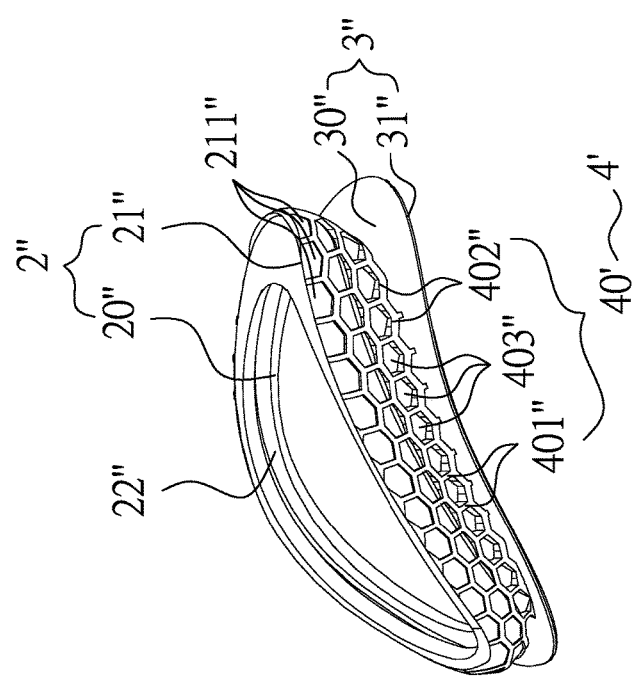
FIGS. 4A to 4C respectively are a perspective view, a top view and a bottom view of a third embodiment of the present invention.
Figure 4B:
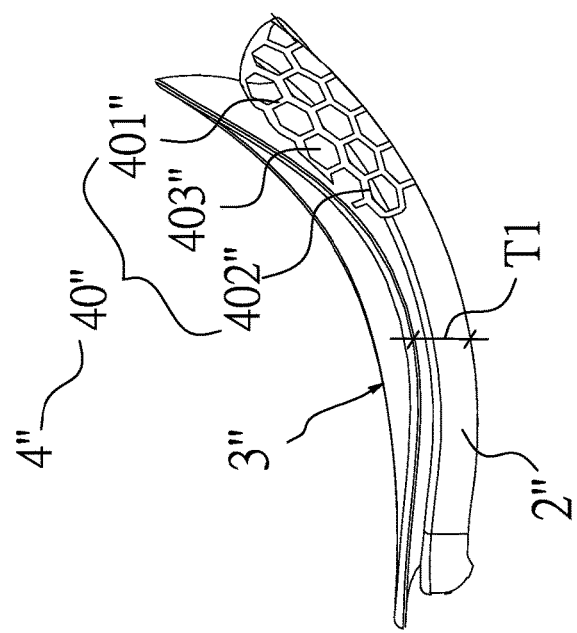
Figure 4C:
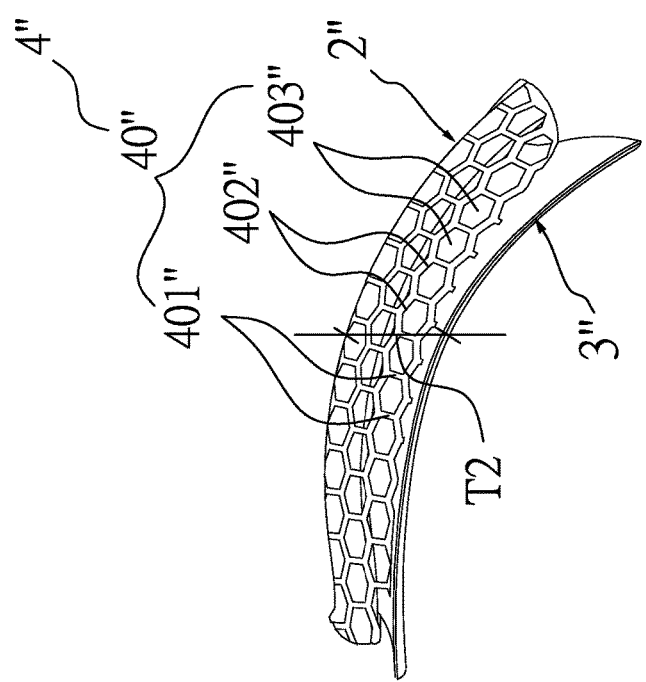
Figure 5:
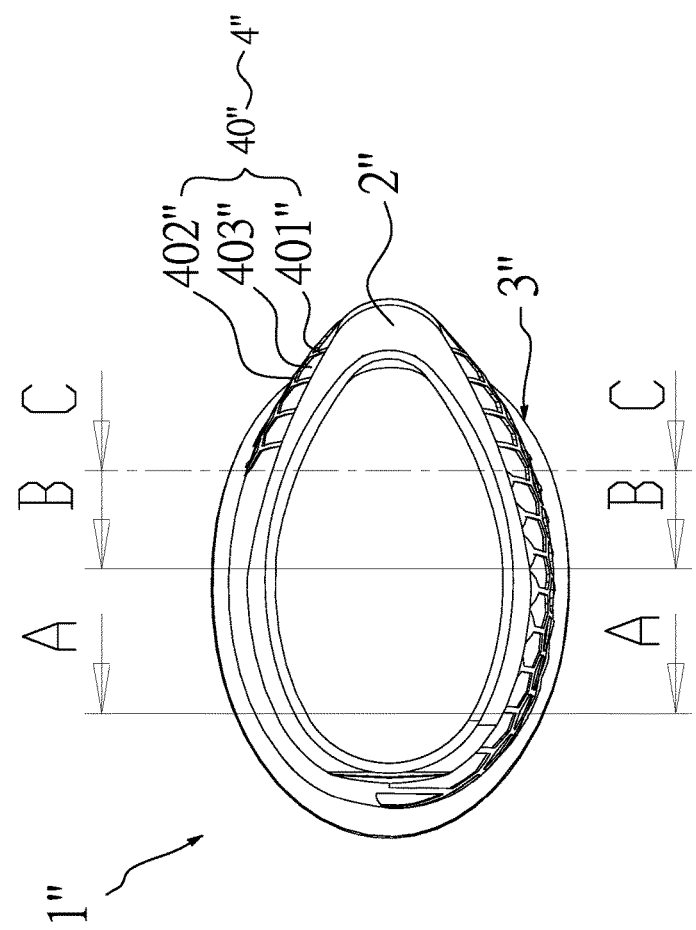
FIG. 5 is a front view of FIG. 4.
Figure 5A:
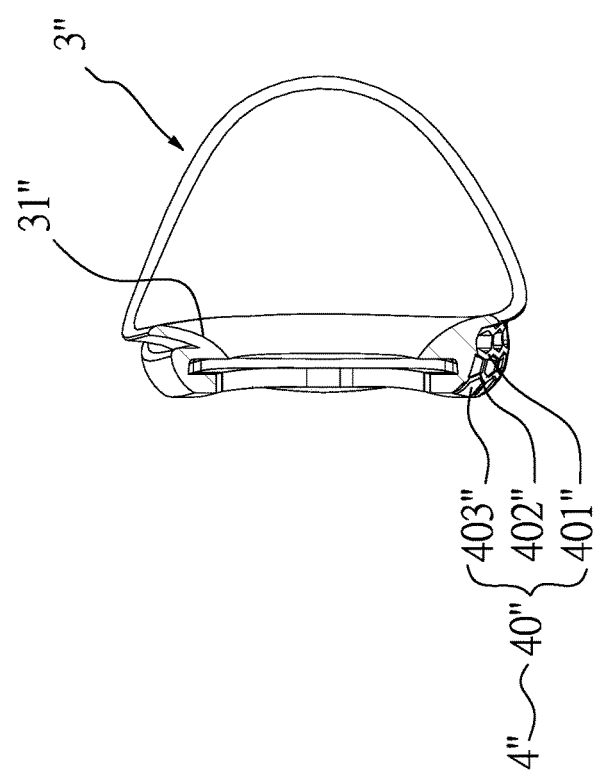
FIGS. 5A to 5C are cross-sectional views respectively taken along line A-A, B-B and C-C of FIG. 5.
Figure 5B:
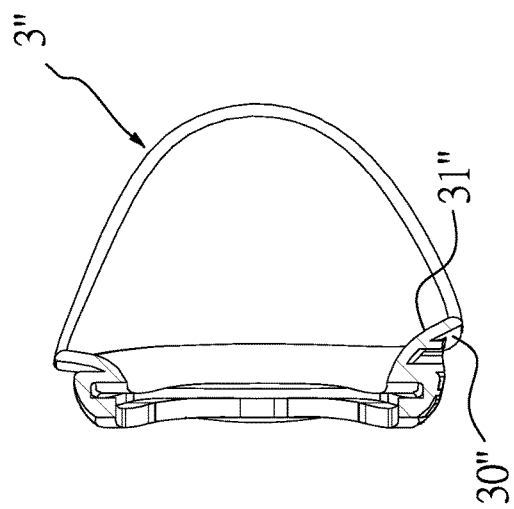
Figure 5C:
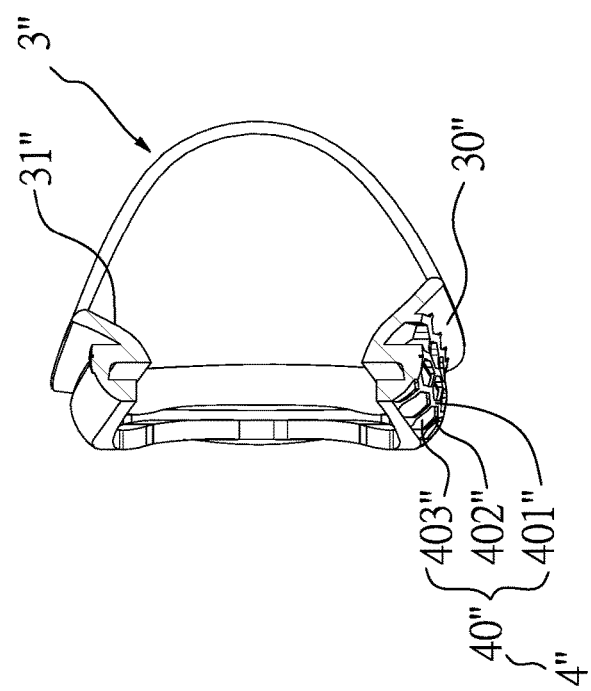

With reference to FIGS. 4A to 4C in view of FIG. 5, and further in view of FIGS. 5A to 5C, which show a third embodiment in accordance with the present invention, a cushion pad 1" of the third embodiment in accordance with the present invention includes a connection frame 2", a face contact portion 3" and a buffer unit 4" as well. The connection frame 2" adapted to connect with a swimming goggle frame which is shown in FIG. 7 is defined with an inner peripheral face 20" and an outer peripheral face 21". A circumferential fitting groove 22" is mounted between the inner peripheral face 20" and the outer peripheral face 21", adapted to receive a circumference of the swimming goggle frame. The face contact portion 3" extending along the inner peripheral face 20" of the connection frame 2" is defined with an outer ring surface 30" and an inner ring surface 31". The inner ring surface 31" is adapted to be in contact with an eye socket of a wearer. The buffer unit 4" is integrally disposed between the inner peripheral face 20" of the connection frame 2" and the outer ring surface 30" of the face contact portion 3". The buffer unit 4" of this embodiment in accordance with the present invention comprises a plurality of compartments 40" each surrounded by two support ribs 401" and a plurality of peripherals 402" to form an opening 403" with a geometric shape, such as polygon. The compartments 40" of the buffer unit 4" of this embodiment are composed of a plurality of polygon openings 403" as being of honeycomb type. The compartments 40" and the openings 403" work together to provide the face contact portion 3" with support and restoring forces against a deformation stress produced between the cushion pad 1" and the wearer's face when the cushion pad 1" is worn, to provide a comfortable engagement with the wearer's face skin without water leakage. Thus, the buffer unit 4" functioned as a buffer is adapted to absorb the deformation stress which is directly acted on a wearer's face around the eye socket when worn, so as to ensure a comfortable engagement with the wearer's face skin without water leakage. In this embodiment together with the first and second embodiments, the cushion pad 1" fitting to an irregular surface contour of the eye socket of the wearer has an axial length T1 corresponding to the eyebrow of the wearer measured from the connection frame 2" to the buffer unit 4" to the face contact portion 3" (as shown in FIG. 4B) smaller than an axial length T2 corresponding to the zygomatic bone of the wearer also measured from the connection frame 2" to the buffer unit 4" to the face contact portion 3" (as shown in FIG. 4C), so as to ensure a compliant engagement with the irregular surface contour of the eye socket of the wearer. Accordingly, besides the compartments 40" and the openings 403" produce the buffering effect, the face contact portion 3" extends in a diverging manner along the irregular surface contour of the eye socket, so as to ensure a comfortable engagement with the wearer's face skin. Furthermore, the compartments 40" scatter at a circumferential direction of the buffer unit 4". In this embodiment, the compartments 40" are arranged partially at a top half of the buffer unit 4" corresponding to the eyebrow of the wearer (as shown in FIG. 4B) and fully at a bottom half of the buffer unit 4 corresponding to the zygomatic bone of the wearer (as shown in FIG. 4C). In addition, the compartments 40" scattering at the circumferential direction of the buffer unit 4" have different sizes. For example, the compartments 40 become larger gradually at a direction from an inner part of the buffer unit 4" corresponding to a nose bridge of the wearer to an outer part of the buffer unit 4" corresponding to an outer eye corner of the wearer, so that the deformation stress which is variable in magnitude along the irregular surface contour of the eye socket of the wearer could be efficiently absorbed in order by the buffer unit 4" by means of the regular arrangement of the compartments 40". Still further, the outer peripheral face 21" of the connection frame 2" is formed with a honeycomb type like pattern 211" thereon to be flush with the compartments 40" of honeycomb type for creating an aesthetic visual feeling.

Referring back to FIGS. 4A and 4B, as mentioned above, the cushion pad 1" fitting to the irregular surface contour of the eye socket of the wearer has the axial length T1 corresponding to the eyebrow of the wearer measured from the connection frame 2" to the buffer unit 4" to the face contact portion 3" smaller than the axial length T2 corresponding to the zygomatic bone of the wearer also measured from the connection frame 2" to the buffer unit 4 to the face contact portion 3", so as to ensure the compliant engagement with the irregular surface contour of the eye socket of the wearer. Besides the compartments 40" and the openings 403" produce the buffering effect, the face contact portion 3" extends in a diverging manner along the irregular surface contour of the eye socket, so as to ensure a comfortable engagement with the wearer's face skin.

Figure 6A:
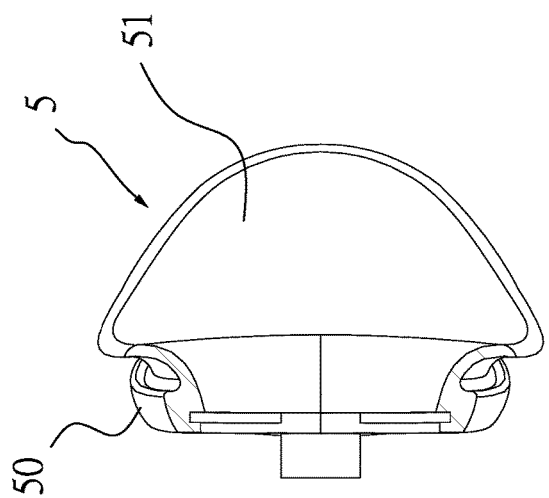
FIGS. 6A and 6B are schematic views respectively in accordance with FIG. 1D and FIG. 5A.
Figure 6B:
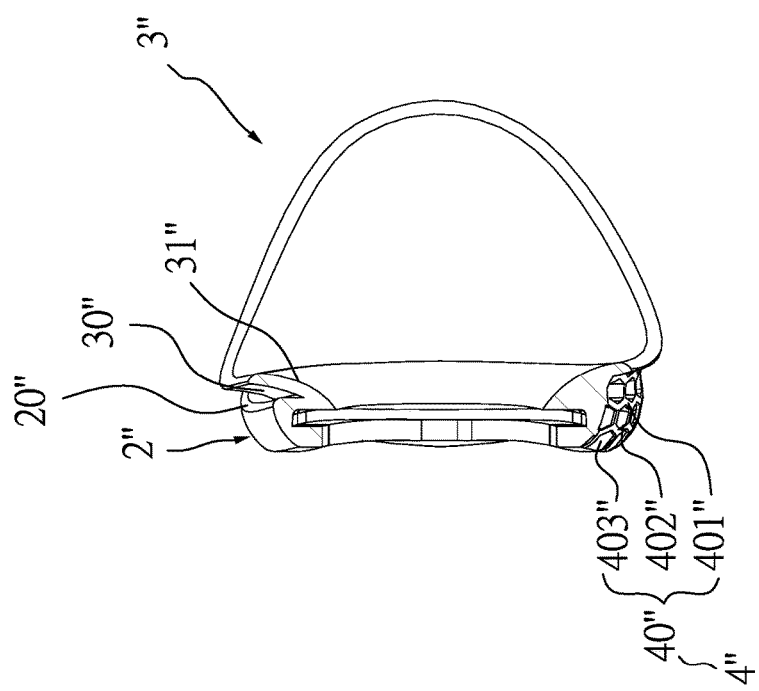

With reference to FIGS. 6A and 6B, the cushion pad 1", as shown in FIG. 6B, is disposed with the compartments 40" and the opening 403", both defined as the buffer unit 4", between the inner peripheral face 20" of the connection frame 2" and the outer ring surface 30" of the face contact portion 3". Thus, the buffer unit 4" functioned as a buffer is adapted to absorb the deformation stress which is directly acted on a wearer's face around the eye socket when worn. In contrast, the conventional cushion pad 5 as shown in FIG. 6A, has no buffer element between the connection frame 50 and the face contact portion 51, so that the face contact portion 51 upon collapse may cause a deformation stress directly acting on the eye socket, thus leading to an uncomfortable feeling and a panda eye also comes out in taking off the swimming goggles.

Figure 8:
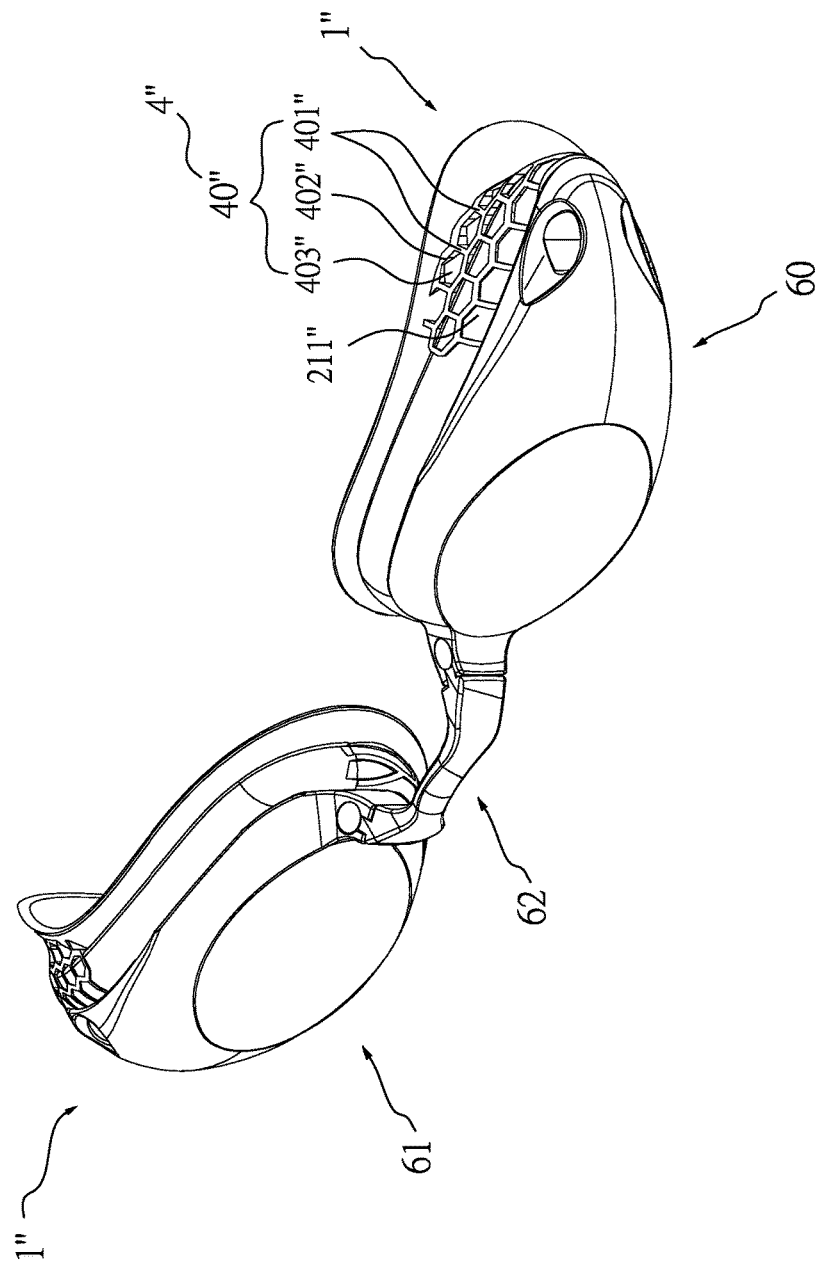
FIG. 8 is an assembled perspective view of FIG. 7.
Figure 9A:
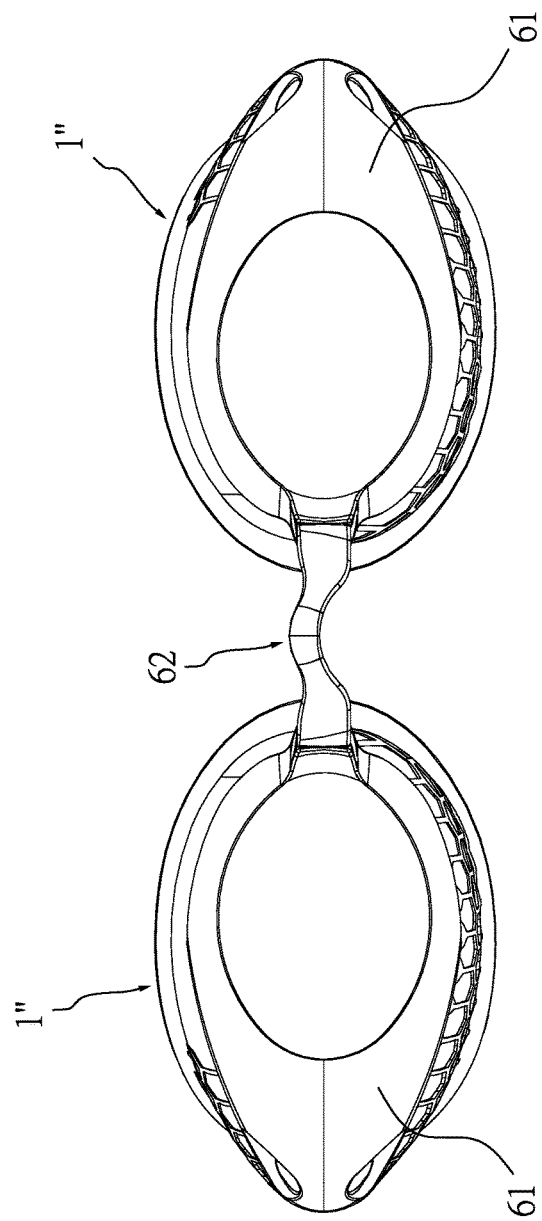
FIGS. 9A to 9C respectively are a front view, a top view, a bottom view of FIG. 8.
Figure 9B:
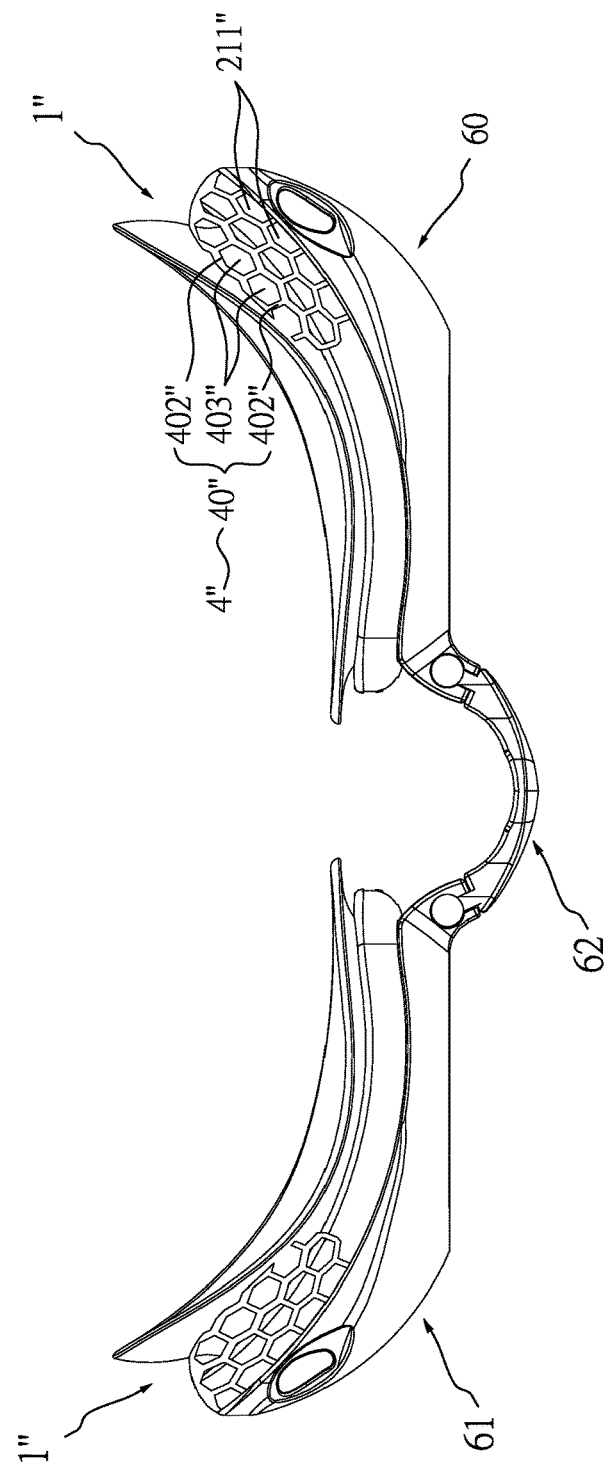
Figure 9C:
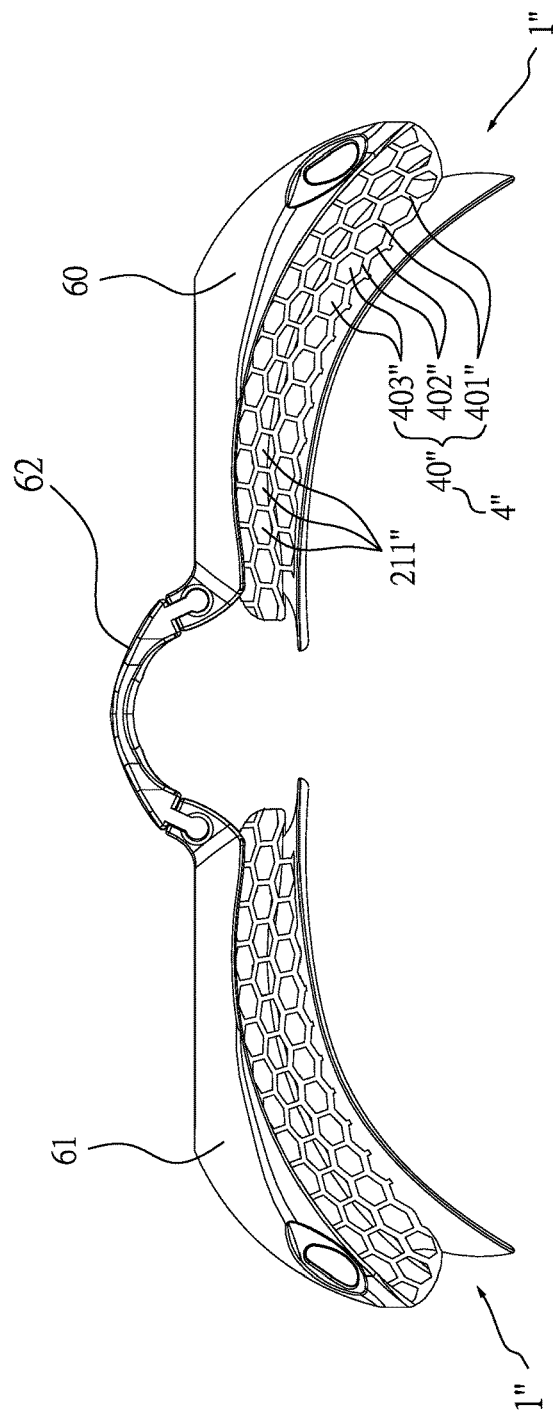

With reference to FIGS. 7 to 9, which shows the cushion pad 1" in accordance with the present invention connecting to left and right frames 60,61 and a connecting element 62 of the swimming goggle frame, the cushion pad 1" overall creates an aesthetic visual feeling after assembly by means of the design of the compartments 40" of the buffer unit 4" together with the honeycomb type like pattern 211" connected thereto, wherein the compartments 40" are arranged partially at a top half of the buffer unit 4" corresponding to the eyebrow of the wearer (as shown in FIG. 9B) and fully at a bottom half of the buffer unit 4 corresponding to the zygomatic bone of the wearer (as shown in FIG. 9C). Under the buffering effect of the compartments 40" and the openings 403", the face contact portion 3" extending along the irregular surface contour of the eye socket provides a flexible and comfortable engagement with the wearer's face skin.

It is understood that the invention may be embodied in other forms within the scope of the claims. Thus the present examples and embodiments are to be considered in all respects as illustrative, and not restrictive, of the invention defined by the claims.

What is claimed is:

1. A swimming goggle cushion pad, being connected to a swimming goggle frame and adapted to be in contact with a wearer's face around an eye socket, wherein the swimming goggle cushion pad comprises:
   a connection frame defined with an inner peripheral face and an outer peripheral face, a circumferential fitting groove being mounted between the inner peripheral face and the outer peripheral face to receive a circumference of the swimming goggle frame;
   a face contact portion extending along the inner peripheral face of the connection frame and defined with an outer ring surface and an inner ring surface; and
   a buffer unit disposed between the inner peripheral face of the connection frame and the outer ring surface of the face contact portion and comprising a plurality of compartments each surrounded by two support ribs and a plurality of peripherals to form an opening;
   wherein the compartments and the opening work together to provide the face contact portion with support and restoring forces against a deformation stress produced between the swimming goggle cushion pad and the wearer's face when worn.

2. The swimming goggle cushion pad of claim 1, wherein the swimming goggle cushion pad adapted to fit to an irregular surface contour of the eye socket of the wearer, wherein an axial length from the connection frame through the buffer unit to the face contact portion at a top side of the swimming goggle cushion pad adapted to correspond to an eyebrow of the wearer is smaller than an axial length from the connection frame through the buffer unit to the face contact portion at a bottom side of the swimming goggle cushion pad adapted to correspond to a zygomatic bone of the wearer, so as to ensure a compliant engagement with the irregular surface contour of the eye socket of the wearer.

3. The swimming goggle cushion pad of claim 1, wherein the compartments are disposed at a circumferential direction of the buffer unit, a number of the compartments is at least three, wherein at least one of the compartments is arranged at a top half of the buffer unit adapted to correspond to an eyebrow of the wearer and at least two of the compartments are arranged at a bottom half of the buffer unit adapted to correspond to a zygomatic bone of the wearer.

4. The swimming goggle cushion pad of claim 1, wherein the compartments are disposed at a circumferential direction of the buffer unit, a number of the compartments is at least three, wherein the compartments at a top half of the buffer unit adapted to correspond to an eyebrow of the wearer are smaller and fewer than the compartments at a bottom half of the buffer unit adapted to correspond to a zygomatic bone of the wearer.

5. The swimming goggle cushion pad of claim 1, wherein the compartments are disposed at a circumferential direction of the buffer unit and have different sizes, wherein the compartments become larger gradually at a direction from an inner part of the buffer unit adapted to correspond to a nose bridge of the wearer to an outer part of the buffer unit adapted to correspond to an outer eye corner of the wearer.

6. The swimming goggle cushion pad of claim 1, wherein the compartments are integrally formed between the inner peripheral face of the connection frame and the outer ring surface of the face contact portion, and each of the compartments is surrounded by two support ribs and a plurality of peripherals to form an opening with a geometric shape, including ellipse, rectangle or polygon, in relation to the compartments correspondingly formed as an elliptical type, a rectangular type or a honeycomb type.

7. The swimming goggle cushion pad of claim 6, wherein the outer peripheral face of the connection frame is formed with a honeycomb type like pattern thereon to be flush with the compartments of the honeycomb type for creating an aesthetic visual feeling.

8. A swimming goggle cushion pad, being connected to a swimming goggle frame and adapted to be in contact with a wearer's face around an eye socket, wherein the swimming goggle cushion pad comprises:
- a connection frame defined with an inner peripheral face and an outer peripheral face, a circumferential fitting groove being mounted between the inner peripheral face and the outer peripheral face to receive a circumference of the swimming goggle frame;
- a face contact portion extending along the inner peripheral face of the connection frame and defined with an outer ring surface and an inner ring surface; and
- a buffer unit disposed between the inner peripheral face of the connection frame and the outer ring surface of the face contact portion and comprising a plurality of support ribs and a plurality of openings between each two adjacent support ribs;
- wherein the support ribs and the openings work together to provide the face contact portion with support and restoring forces against a deformation stress produced between the swimming goggle cushion pad and the wearer's face when worn.

9. The swimming goggle cushion pad of claim 8, wherein the swimming goggle cushion pad is adapted to fit to an irregular surface contour of the eye socket of the wearer, wherein an axial length from the connection frame through the buffer unit to the face contact portion at a top side of the swimming goggle cushion pad adapted to correspond to an eyebrow of the wearer is smaller than an axial length from the connection frame through the buffer unit to the face contact portion at a bottom side of the swimming goggle cushion pad adapted to correspond to a zygomatic bone of the wearer, so as to ensure a compliant engagement with the irregular surface contour of the eye socket of the wearer.

10. The swimming goggle cushion pad of claim 9, wherein the support ribs are integrally arranged at intervals between the inner peripheral face of the connection frame and the outer ring surface of the face contact portion, wherein the support ribs are disposed at a circumferential direction of the buffer unit, a number of the support ribs is at least five, wherein at least two of the support ribs are arranged at a top half of the buffer unit adapted to correspond to the eyebrow of the wearer and least three of the support ribs are arranged at a bottom half of the buffer unit adapted to correspond to the zygomatic bone of the wearer.

11. The swimming goggle cushion pad of claim 8, wherein the support ribs and the openings are disposed at a circumferential direction of the buffer unit and have different sizes, wherein the support ribs and the openings become longer and wider gradually at a direction from an inner part of the buffer unit adapted to correspond to a nose bridge of the wearer to an outer part of the buffer unit adapted to correspond to an outer eye corner of the wearer.

* * * * *